(12) United States Patent
Werblin

(10) Patent No.: US 7,437,303 B2
(45) Date of Patent: Oct. 14, 2008

(54) METHOD AND SYSTEM FOR IMPLEMENTING AND TRACKING COST-SAVING MEASURES IN HOSPITALS AND COMPENSATING PHYSICIANS

(75) Inventor: Theodore Paul Werblin, Bluefield, WV (US)

(73) Assignee: Physician Hospital Services, LLC, Colorado Springs, CO (US)

( * ) Notice: Subject to any disclaimer, the term of this patent is extended or adjusted under 35 U.S.C. 154(b) by 953 days.

(21) Appl. No.: 10/384,114

(22) Filed: Mar. 7, 2003

(65) Prior Publication Data

US 2003/0171955 A1   Sep. 11, 2003

Related U.S. Application Data

(60) Provisional application No. 60/362,343, filed on Mar. 7, 2002.

(51) Int. Cl.
  *G06Q 50/00* (2006.01)
  *G06Q 40/00* (2006.01)
(52) U.S. Cl. .............................................. 705/2; 705/4
(58) Field of Classification Search .................. 705/2–4
  See application file for complete search history.

(56) References Cited

U.S. PATENT DOCUMENTS

| | | | | |
|---|---|---|---|---|
| 5,365,425 | A * | 11/1994 | Torma et al. | 705/2 |
| 5,778,345 | A * | 7/1998 | McCartney | 705/2 |
| 5,835,897 | A * | 11/1998 | Dang | 705/2 |
| 5,845,254 | A * | 12/1998 | Lockwood et al. | 705/2 |
| 7,003,470 | B1 * | 2/2006 | Baker et al. | 705/1 |
| 7,389,245 | B1 * | 6/2008 | Ashford et al. | 705/2 |
| 7,398,217 | B2 * | 7/2008 | Lewis et al. | 705/2 |
| 2001/0051765 | A1 * | 12/2001 | Walker et al. | 600/300 |
| 2002/0082963 | A1 * | 6/2002 | Corvin | 705/36 |
| 2002/0099585 | A1 * | 7/2002 | Locke | 705/7 |
| 2002/0111826 | A1 * | 8/2002 | Potter et al. | 705/2 |
| 2002/0123905 | A1 * | 9/2002 | Goodroe et al. | 705/2 |
| 2003/0163352 | A1 * | 8/2003 | Surpin et al. | 705/2 |
| 2006/0149596 | A1 * | 7/2006 | Surpin et al. | 705/2 |

OTHER PUBLICATIONS

Miller, Health System Integration: A Means To An End, 1996, Health Affairs, vol. 15, No. 2, 92-106.*

(Continued)

*Primary Examiner*—C Luke Gilligan
*Assistant Examiner*—Tran Nguyen
(74) *Attorney, Agent, or Firm*—Kent A. Lembke; Marsh Fischmann & Breyfogle LLP

(57) ABSTRACT

A method and system whereby one or more physicians work with a hospital to create savings and are compensated in a manner that is legal and acceptable to the United States Office of Inspector General of the Health and Human Services Department (OIG). In one example, a physician is paid to help implement cost-saving measures by the hospital or a consultant to the hospital under a personal service contract based upon an OIG safe harbor provision. In another example, the hospital can compensate physicians of its choosing for otherwise uncompensated services under the same safe harbor provision. Projected savings can be taken into consideration by the hospital when it determines how much it can afford to pay to physicians, although payments are made irrespective of whether projected savings are realized.

6 Claims, 3 Drawing Sheets

OTHER PUBLICATIONS

Dudley et al., Health Policy 2001, 2001, New England Journal of Medicine, vol. 344: 1087-1092.*

Cost Control Incented Many Ways Despite OIG Ruling on Gainsharing, Apr. 12, 2000. Physician Compensation Report. [Retrieved on Nov. 9, 2004]. http://www.findarticles.com.*

Palmquist, Physician-partnering models offer legal alternatives to traditional gain-sharing, Nov. 1, 2000, Healthcare Financial Management, vol. 54, No. 11, p. 58-63.*

Kristal, 1998-1999 SAEM Emergency Medicine Faculty Salary and Benefits Survey, Dec. 1999, Academic Emergency Medicine, vol. 6, No. 12, p. 1261-1271.*

Gosden, How should we pay doctors? A systematic review of salary payments and their effect on doctor behaviour, 1999, Oxford Journal: QJM, vol. 92, No. 1, p. 47-55.*

Giokas, Greek hospitals: how well their resources are used, Feb. 2001, Omega, vol. 29, No. 1, p. 78-83.*

"Gainsharing Arrangements and CMPs for Hospital Payments to Physicians to Reduce or Limit Services to Beneficiaries," [online] [retrieved on 6/5/103]. Retrieved from the Internet URL //oig/hhs.gov/fraud/docs/alertsandbulletins/gainsh/htm, pp. 1-9.

Karl A. Thallner, Jr., Esq. "OIG approves hospital-physician gainsharing," [online] [retrieved on Feb. 28, 2003]. Retrieved from the Internet URL physiciansnews.com/law/701.html, pp. 1-8.

Stan Mendenhall, "The unintended results of "outlawing" gainsharing," Orthopedic Network News, vol. 10, No. 3, Jul. 1999, pp. 1-1.

D. McCarty Thornton, OIG Advisory Opinion No. 01-1, pp. 1-16.

* cited by examiner

METHOD AND SYSTEM FOR IMPLEMENTING AND TRACKING COST-SAVING MEASURES IN HOSPITALS AND COMPENSATING PHYSICIANS

RELATED APPLICATIONS

This application claims priority to U.S. Provisional application Ser. No. 60/362,343 Filed on Mar. 7, 2002, which is incorporated herein by reference.

BACKGROUND OF THE INVENTION

1. Field of the Invention

The present invention relates, in general, to systems and methods for hospital cost and performance management, and, more particularly, to software, systems and methods for generating cost savings in hospitals, compensating physicians for services provided, and compensating physicians for otherwise uncompensated services based upon the assumption that projected savings will enhance the financial resources of the hospital thereby enabling the compensation.

2. Relevant Background

Hospitals remain a primary avenue for providing health care in the United States. Although some hospitals employ staff physicians, in most cases the physician is not an employee, and contracts with the hospital for privileges to use the hospital facilities. The contracted-for privileges allow the physician to have patients admitted, use operating rooms and other hospital equipment and facilities, and use shared hospital personnel such as nurses, technicians and the like. The terms of these contracts vary, however, it is typical for such contracts to obligate the physician to provide certain uncompensated services for the hospital. Independent physicians in the United States historically have provided certain uncompensated services to hospitals where they have privileges to admit and treat patients.

Hospitals that receive Medicare funding are required by the U.S. Government under, for example, the Emergency Medical Treatment and Active Labor Act (EMTALA), also titled Consolidated Omnibus Budget Reconciliation Act (COBRA), to provide emergency care to all patients regardless of the patient's ability to pay. This often results in hospitals providing services to some patients without compensation, which is often called "charity care." It is common practice for hospitals, in-turn, to require physicians that have privileges at their hospital to provide care to hospital patients who cannot pay without compensation.

It is also common for hospitals to expect and/or require physicians with privileges, especially specialists, to provide on-call services to the hospital emergency room. While on-call, the physician agrees to remain accessible to provide services to the hospital on immediate or short-term notice, whether or not such services are actually needed. While the physicians may be compensated for services actually rendered while on-call, they are not compensated by the hospital simply for being on-call.

In addition, most hospitals expect and/or require physicians to serve on various hospital committees, participate in employee training, and/or attend to other managerial tasks without compensation. Active and enthusiastic participation in such committees are important mechanisms for improving health care services. However, because these tasks are uncompensated it is sometimes difficult to engender the enthusiastic and active participation of the best physicians that are available.

Prior to the advent of what is commonly referred to as "managed care", physicians were compensated for most of their services at a rate that economically allowed them to provide the above-mentioned services for free. Reimbursement rates to physicians by. Medicare/Medicaid, managed-care programs and other insurance programs generally have been significantly lowered in the past several years. At the same time, costs of doing business such as insurance, marketing, equipment, office space and the like have increased. These factors encourage physicians to spend more of their time providing compensable services (e.g., treating patients) and less time in non-compensable activities. As a result, physicians have less ability to continue to provide charitable services, participate on committees, and the like, that are not compensated. Hence, to continue to achieve the benefits that have historically been provided by uncompensated physician services, there is a need for systems and methods that provide additional compensation for services that have historically been uncompensated.

Hospitals are also under economic pressures due to lower reimbursement rates for their facilities, as well as the burdens of providing uncompensated services such as charity care. Further, the costs of operating a hospital continue to climb. Hence, hospitals often do not have the financial resources to compensate physicians for the traditionally uncompensated services. In many cases, the conflicting economic pressures between hospitals and physicians is causing a strain on the relationship. Both hospitals and physicians will benefit from a solution to these problems.

Another significant effect of these problems is that physicians have little incentive to commit the time and energy required to identify and validate various efficiency improvement activities within a hospital. Identifying, developing, and testing new procedures and/or equipment is often an intensive process that benefits from significant physician involvement. However, since such involvement is not compensated, the commitment to implement such procedures is waning. Hospitals have a difficult time pursuing these efficiency improving activities without physician involvement, and have an even more difficult time in encouraging adoption of new processes and tools when the physicians were not involved in the development phase.

A significant obstacle in a practical solution has been the lack of funds to provide additional compensation and incentives for the activities that have been traditionally uncompensated. Generally, physicians are prohibited from receiving payments, or "gainsharing", from clinical decisions they directly make that would create cost savings. In July 1999 the Office of Inspector General (OIG) within the Health and Human Services Department issued a Special Advisory Bulletin that stated broad prohibitions against any form of gainsharing which had the effect of putting an end to efforts to build incentive-based cost-savings programs. Gainsharing is a term used to refer generally to a variety of types of financial arrangements between physicians and hospitals that are intended to encourage the physicians to deliver quality care in a cost-effective manner. However, in that same Special Advisory Bulletin the OIG stated that:

" . . . We note, however, that hospitals may align incentives with physicians to achieve cost savings through means that do not violate section 1128A(b)(1) of the Act. For example, hospitals and physicians may enter into personal services contracts where hospitals pay physicians based on a fixed fee that is fair market value for services rendered, rather than a percentage of cost savings. Such contracts must meet the requirements of the anti-kickback statute (section 1128B(b) of the Act) . . . . "

Hence, the OIG carved out a "safe harbor" of permissible incentive programs largely ignored and undiscovered.

In January, 2001, the OIG issued a positive opinion with respect to a cost-saving program that described a narrow set of circumstances in which physicians could receive gainsharing payments. Until the development of the present invention, this was the only example of such a transaction receiving a positive advisory opinion from the OIG. This OIG opinion is commonly referred to as the "01-1 opinion". This particular opinion was limited to gainsharing payments for a given set of procedures and further was limited by how much and how long such payments could be made. Hence, operation in accordance with the 01-1 opinion was only a partial solution to the above-identified problems.

Hence, health care economics and human nature suggest that some form of incentive plan that rewards physicians for participating in cost-savings programs is an effective way to provide health care more efficiently. However, concerns over gainsharing have made prior implementations of such incentive programs impossible. As a result, many inefficiencies continue, creating financial strain on both physicians and hospitals, which in turn cuts into the willingness and ability of all participants in the health care system to provide various services such as that have been traditionally uncompensated. Accordingly, a solution is needed in the form of systems and methods that provide adequate incentives in a legally compliant manner.

SUMMARY OF THE INVENTION

Briefly stated, the present invention involves systems and methods whereby one or more physicians work with a hospital to create savings and are compensated in a manner that is legal and acceptable to the United States Office of Inspector General of the Health and Human Services Department (OIG). In one example, a physician is paid to help implement cost-saving measures by the hospital or a consultant to the hospital under a personal service contract based upon an OIG safe harbor provision. In another example, the hospital can compensate physicians of its choosing for otherwise uncompensated services under the same safe harbor provision. Projected savings can be taken into consideration by the hospital when it determines how much it can afford to pay to physicians, although payments are made irrespective of whether projected savings are realized.

DETAILED DESCRIPTION OF THE PREFERRED EMBODIMENTS

Figure 1:
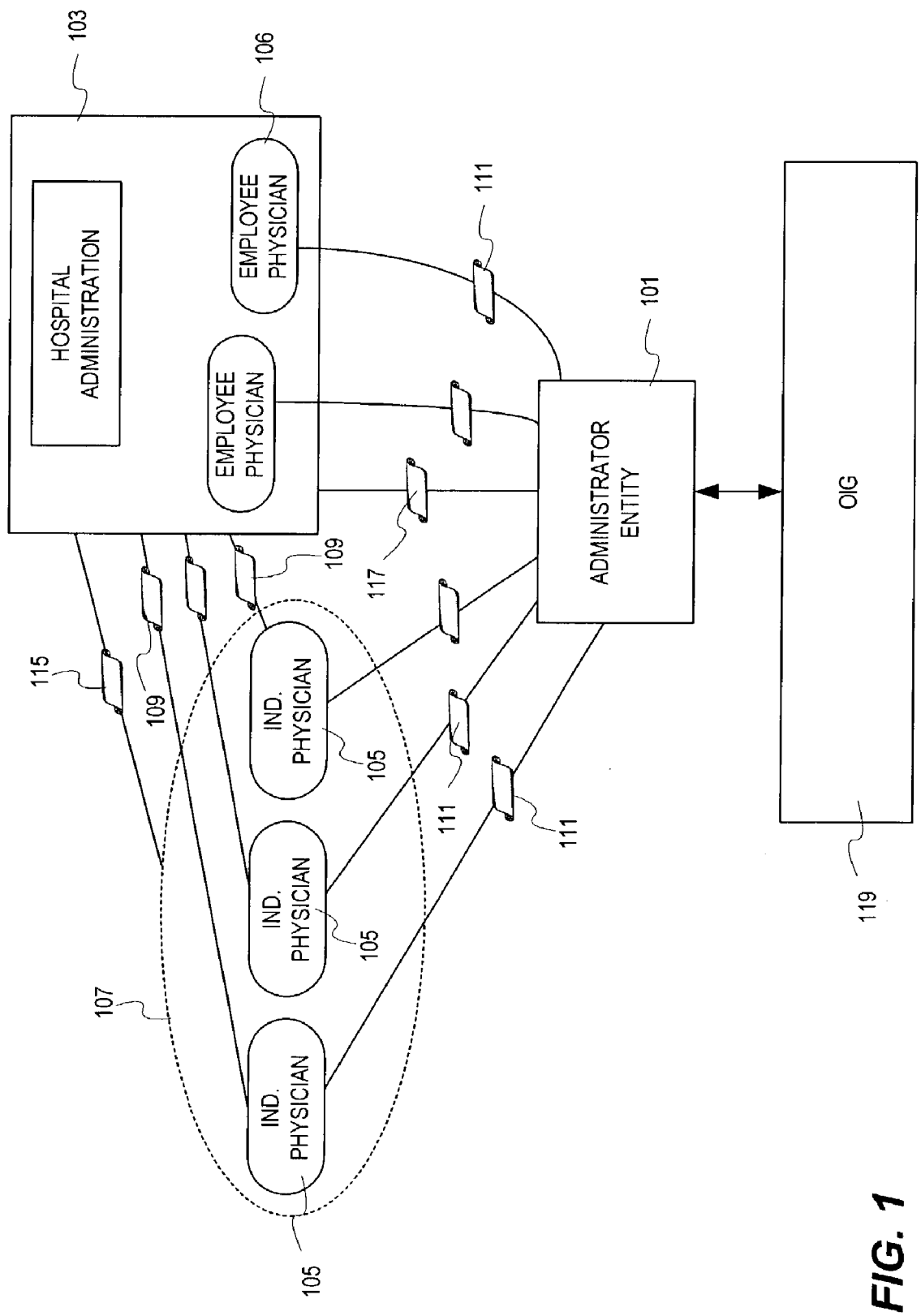
FIG. 1 illustrates various entities involved in an implementation of the present invention and contractual relationships between those entities.

The invention is directed toward methods and system for implementing and managing a program to create cost savings in hospital functions that engenders active participation of physicians by legally compensating physicians either for their services to help implement cost-saving measures and/or compensating physicians for otherwise uncompensated services. Payments to physicians are carefully structured to fall under a personal services safe harbor as defined by the Office of the Inspector General (OIG) such that said payments are not considered gainsharing and do not violate anti-kickback statutes. The present invention is intended to create new sources of funds to help hospitals reward physicians to participate in the program and to provide a source of funds to enhance the hospital's financial conditions such that it can better afford to compensate physicians for otherwise uncompensated services. The present invention may also provide a new source of profits for the hospital.

1. Development History.

The inventor of the present invention, Dr. Theodore P. Werblin, developed one prior system at Princeton Community Hospital Physicians/Hospital Advocates, LLC (PCH) in Princeton, W.Va. The physicians at PCH expressed dissatisfaction to the hospital administration regarding the uncompensated services problem. The parties at first were unable to find a source of funding to address the problem. The Department Chair of Surgery, and inventor of the present invention, suggested a potential solution of physicians working with the hospital to create savings from hospital functions and using a portion of those savings as a source of funding to at least partially pay for uncompensated physician services. The concept was based in part upon his experience of creating savings within the surgeries he performs. It was felt that his experience could be expanded to other operations to create a significant source of savings. A group of physicians at PCH formed a company called PCH Advocates LLC to work out a cost-saving program with PCH.

The PCH management agreed to the concept as long as the idea did not violate Federal regulations or laws governing this type of transaction and was cost neutral to the hospital. The PCH plan was different from the plan approved in the OIG 01-1 opinion in that the PCH plan contemplated using the savings to provide compensation to physicians for various services performed that typically are not compensated and to use the savings for this purpose indefinitely. The PCH parties applied for an opinion from the OIG on their particular plan. After receiving a positive verbal response initially from the OIG, the request was put on hold due to several uncertainties and eventually withdrawn.

It was recognized that the formal OIG opinion process, while viable, would likely result in specific solutions that would require a new OIG opinion for each implementation instance, and new opinions for any variations and improvements. While investigating alternatives to the formal opinion process, it was discovered a method to structure payments to physicians under a safe harbor provision such that the payments would not be considered gainsharing. This safe harbor can be used to provide direct compensation for services provided by physicians to implement cost-saving measures. However, the safe harbor, by itself, does not suggest any mechanism for funding these allowed payments to physicians. Also, such payments, although helpful, are limited and do not solve the uncompensated services problem.

2. Preferred Implementation.

The present invention presents a new structure that uses an existing safe harbor provision to provide compensation to physicians for services provided to help implement a cost-management program in a hospital and in addition to cover payments made for otherwise uncompensated services. A key to success is the ability to incorporate data regarding the potential for cost savings into the new structure. The present invention satisfies gainsharing regulations that prevent making payments to a physician that are directly or indirectly tied to actual cost savings achieved by that physician. However, the present invention recognizes that prospective information about the expected financial benefit that is projected to arise from a particular cost-savings measure can be valuably used in the processes of prospectively assessing the costs and benefits of such a program, and in evaluating how much the hospital can afford to pay physicians, consultants, and others to implement the cost-savings measure.

It is contemplated that in view of the hospitals improved financial position, the hospital will be able to afford to provide the compensation allowed by the safe harbor provision. This solution is believed to address significant issues in compensating traditionally uncompensated services without running afoul of gainsharing rules. By preventing physician compensation from being tied to actual cost-savings measures, the sprit and letter of anti-gainsharing regulations are promoted as instantaneous physician decisions will not affect compensation to that physician. At the same time, the ability to consider the prospective financial benefits and generate productive incentives is created by the present invention.

Current safe harbor provisions allow payments to physicians taking projected cost savings into consideration for services such as emergency room on-call so long as the payments 1) are not contingent upon savings, 2) the payments do not exceed market rates, 3) the payments are fixed fee and 4) the contract has a term of at least one year.

Implementing cost-management programs with the assistance of physicians may provide a new source of funds for hospitals, making financial resources available to hospitals so that they can pay for services that are no longer available at no cost. In the United States, the federal government prohibits physicians from receiving a portion of savings they help to create, a practice known as gainsharing. The present invention contemplates a system with two independent prongs that together provide appropriate and legally compliant incentives to improve hospital efficiencies.

A first class of payments involves a payment that can be directly tied to a physician's performance of services to assist the hospital to develop and implement cost-saving measures. These payments are designed to comply with one or more OIG opinions that create a specific permission for those payments. Even in cases where an OIG opinion is obtained, authorization for the plan may be under the safe harbor provision, but clarified through an informal opinion that using projected savings to consider its potential impact on hospital finances is permissible. Independently, a second class of payments involves a payment that is authorized by the safe harbor provisions of the anti-gainsharing regulations (i.e., payments that are independent of any cost-saving program). This second class of payments are indirectly made possible by the improved financial position of a hospital that results from cost savings program successes, but are not directly funded by actual or anticipated cost savings. The cooperation of these two payment types creates a unique system for managing hospital cost savings programs.

In the second class of payments the hospital alone determines which physicians are compensated and how much to compensate them for services such as emergency room on-call, so long as the compensation does not exceed market rate. Although the hospital could certainly divert funds resulting from cost savings to other purposes, it is contemplated that hospitals recognize that it is in the financial interest of the hospital to compensate physicians for otherwise uncompensated services to maintain a good working relationship with physicians, and to encourage optimum performance of the services they demand from physicians. Indirectly, the second class of payments reinforce that it is in the interest of physicians to do their best to help the hospital to save money so that the hospital is in a better financial position to afford to pay for otherwise uncompensated services.

Because the two methods of physician payment are not linked, it is possible for some physicians who do not participate in the cost-saving program to be paid for ER on-call or some physicians who do participate in the cost-saving program to not be paid for ER on-call. However, in many cases it is likely that physicians who participate in the cost-saving program will also be paid for ER on-call because of the natural relationship between the two situations.

3. Specific Example.

An important feature of the invention is how to structure both classes of payments so that they are not considered gainsharing or violate the anti-kickback statutes. The present invention teaches methods to justify and increase the payments in light of the cost-management program.

As shown in FIG. 1, four important entities are involved in the specific example. Hospital 103, independent physicians 105, an independent entity 101, and the office of inspector general 119. Additionally, employee physicians 106, which are employees of hospital 103, may be involved in particular implementations.

a) Physician Role

The present invention is primarily intended for physicians 105/106 that are specialists, such as orthopedic and cardiac surgeons, anesthesiologists, and other specialists that have a private practice with privileges to admit and/or treat patients at a given hospital 103. The present invention can also apply to non-surgical physicians but it is expected that specialists that work frequently or exclusively in a hospital environment (as opposed to primary care physicians) will typically generate the most cost savings to a hospital 103. However, it is contemplated that in some applications non-specialists may also generate significant savings in which case the present invention can be readily modified to include such participants. For example, a bonus can be paid to physicians 106 that are employed by the hospital, but the payments for services would be for services provided for which the physician is not already compensated otherwise.

Physicians 105/106 enter into a contract 115 with the hospital 103 and a contract 111 with the administrative entity 101 to implement the present invention. The physician 105 will be responsible for making clinical decisions related to patient care that may create cost savings. As appropriate, the physicians 105/106 and hospital administration would establish an internal review committee to evaluate and approve cost-savings measures. It is expected that the administrator entity 101 will provide an inventory of pre-approved cost-savings measures that can potentially be used in any given implementation, but the particular physicians 105/106 at each hospital 103 determine what is appropriate for their situation and make decisions on an ongoing basis for each patient. At any time, physicians can identify new cost-saving measures and submit them to the hospital 103 and/or administrator 101 for consideration under this program. New measures can be made available system-wide so that they benefit multiple hospitals 103.

In the case of the first class of payments described above, only one physician 105/106 is required to implement the present invention at a given hospital 103. In the case of the second class of payments, a larger group with sufficient diversity may be required in order to use the second type of payment for otherwise uncompensated services. A program can be implemented by starting with the first class payments and then evolving into the second payment class once sufficient doctors are involved. The second type of payment is more useful and will promote longevity of the system. Other physicians 105/106 can join at any time thereafter. Either the hospital 103 or the administrative entity 101, under contract to the hospital 103, can compensate physicians 105/106 for services provided to help implement cost-saving measures. Although the hospital can use actual savings as well as projected savings to determine if and how much the hospital can afford to compensate physicians, these payments are explicitly not contingent upon actual savings achieved.

Hospital 103 is typically organized as an independent business entity, which may be for-profit or non-profit, and may be any of a variety of business organizational forms. Hospital 103 provides various facilities, services, employees, and administration that can be used by both independent physicians 105 and employee physicians 106 to provide care to patients. In a typical situation, hospital 103 enters into contracts 109 with independent physicians 105 to grant privileges to independent physicians 105 that enable the independent physicians 105 to admit and treat patients using the hospital facilities. The hospital benefits from such contracts because it charges patients for these services and facilities. In most cases, independent physicians 105 are not paid under these contracts with the hospital. Instead, physicians 105 are paid by their patients (or their insurance companies) directly. The hospital also benefits from contracts with physicians 105 by requiring independent physicians 105 to provide certain services such as "on-call", charity services, administrative services, and the like. An important feature of the present invention is that mechanisms are implemented to enable the physicians 105 and 106 to be paid for such services.

One or more physicians 105/106 that are either employed or have privileges at a given hospital agree to implement the present invention. These agreements are implemented, for example, by supplementary contracts 115 which may be implemented between hospital 103 and individual physicians 105/106, or between hospital 103 and one or more groups 107 to which physicians 105/106 belong. It is preferred that the physicians at a given hospital organize as a group 107; however, it is possible to enter into individual contracts 115 or in one or more groups 107 smaller than the whole, although such an implementation would be less efficient. In the case of employee physicians 106, the agreements can be implemented by amendments to or changes to employment agreements between hospitals 103 and employee physicians 106. Administrative entity 101 may assist the parties to finalize the details of the contracts between the physicians 105/106 and hospital 103 so that these agreements are preferably in a form that complies with any formal/or informal opinion(s) and regulations obtained by administrative entity 101 and OIG 119.

b) Hospital Role

A given hospital 103 is a major participant in the operation of present invention. The cost savings mostly will be derived from changes in supplies purchased by and procedures performed at the hospital 103. Hospital 103 enters into a contract 115 with one or more physicians 105/106 that have privileges at the hospital to implement the present invention. Hospital 103 plays a key role in helping to establish baseline costs, reviewing and approving cost-saving measures, supporting implementation of the measures, and tracking cost savings.

c) Administrative Entity Role

Administrator entity 101 is provided as an independent legal entity such as a corporation, limited liability company (LLC), or other business form that meets the needs of a particular application. Administrator entity enters into contract(s) 117 with the hospital 103 to, for example, establish and administer the implementation of the present invention with that hospital 103, or to provide other services for hospital 103. Contract 117 may provide for payment to entity 101 either on a negotiated fee basis and/or can be paid a percentage of the savings generated on an ongoing basis. Administrator entity 101 will generally provide model contracts (e.g., models for contracts 115, 111 and the like) an inventory of cost-saving measures and techniques, as well as general guidance on how to identify and implement additional cost-saving measures. Administrator entity 101 may also provide services to help determine baseline costs, implement the cost-saving measures, track savings, determine allocations, collect the portion of the savings, make payments to physicians, and audit the program to ensure compliance regulatory requirements established by OIG 119.

Administrative entity 101 and one or more physicians 105/106 enter into contracts 111 to implement the present invention at hospital 103. Administrative entity 101 will work with the physicians 105/106 according to the terms of contract 117 between administrative entity 105 and hospital 103. In a specific example, contract 117 involves the implementation of cost-saving measures and administration of the implementation, accounting, and management of those cost-savings measures in accordance with any applicable OIG opinions and regulations as well as the safe harbor provision discussed above.

OIG 119 continues a traditional regulatory and oversight role involving various aspects of hospital operations, which may change over time or may be implemented in other regulatory or governmental bodies. OIG 119 oversees various aspects of physician behavior to enforce various laws and regulations affecting how physicians perform their duties. Administrative entity 101 works closely with OIG 119 to ensure compliance with the OIG rules and regulations to implement the present invention. A significant advantage of the present invention is that the vagaries and changes normally associated with the regulatory environment can be monitored closely by independent entity 101 on behalf of physicians 105/106 and hospitals 103 which traditionally have had little time or inclination to do so. This enables administrative entity 101 to develop expertise and relationships necessary to obtain special permissions, granted in the form of informal and format opinions, from OIG 119 that authorize specific relationships between hospitals 103 and physicians 105/106. Alternatively and in addition, current regulations provide various provisions (e.g., safe harbor provisions) that provide more general authorization to relationships between hospitals 103 and physicians 105/106. Administrative entity 101 monitors these general authorizations as well.

4. Exemplary Operation.

Figure 2:
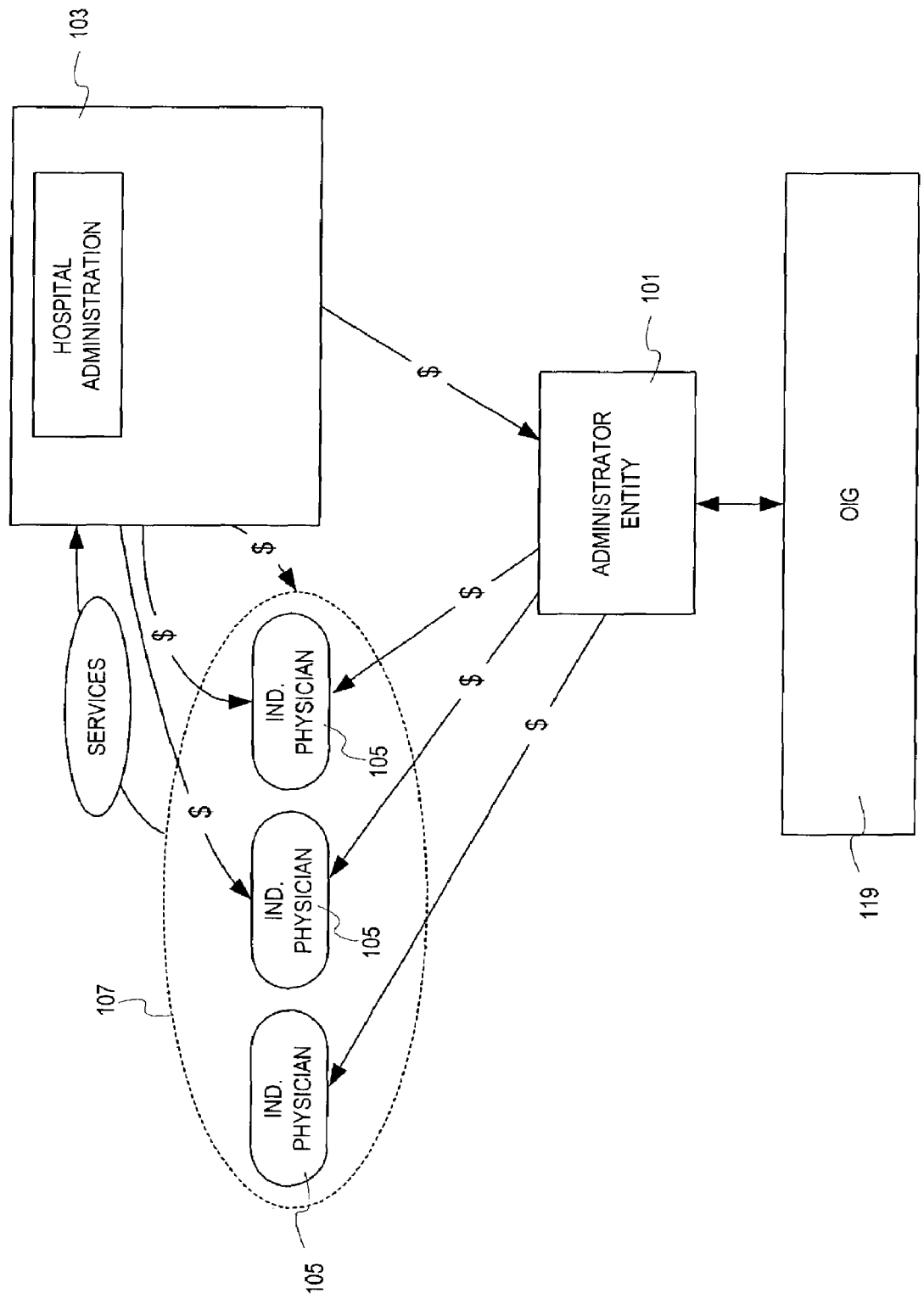
FIG. 2 illustrates the entities of FIG. 1 and the operational relationships between those entities.

FIG. 2 illustrates operational features of an embodiment of the present invention adopting the structures and relationships described in reference to FIG. 1. As a result of participation in the present invention, physicians 105/106 may be paid by administrative entity 101 as appropriate for services provided to help the hospital implement cost-savings measures. In the case of payments to physicians 105 for providing consulting services to help implement cost-saving measures, agreements can either be directly between the hospital and individual physicians or between hospital 103 and one or more groups of physicians (e.g., supplemental contracts 115 in FIG. 1). Administrator 101 can also act as an intermediary for the hospital to manage these contracts.

Moreover, physicians 105/106 may participate in payments made by the hospital 103 for otherwise uncompensated services. These new payments may in part be made possible because the cost saving program has helped hospital 103 to better afford these payments. Under current regulatory requirements, in the case of payments to physicians 105 for otherwise uncompensated services, such as ER on-call, those payments should be structured so there is no connection between savings generated by that physician 105. It is recommended that a diverse group of physicians 105/106 form a group 107 to provide services (e.g., ER on-call services) under a single contract with hospital 103. The physicians determine how to allocate payments amongst themselves based upon services provided with no ties to savings generated. In some cases, members of the group may help generate savings and not be paid for ER on-call, or not generate savings and be paid for ER on-call.

5. Optional and Alternative Features.

Figure 3:
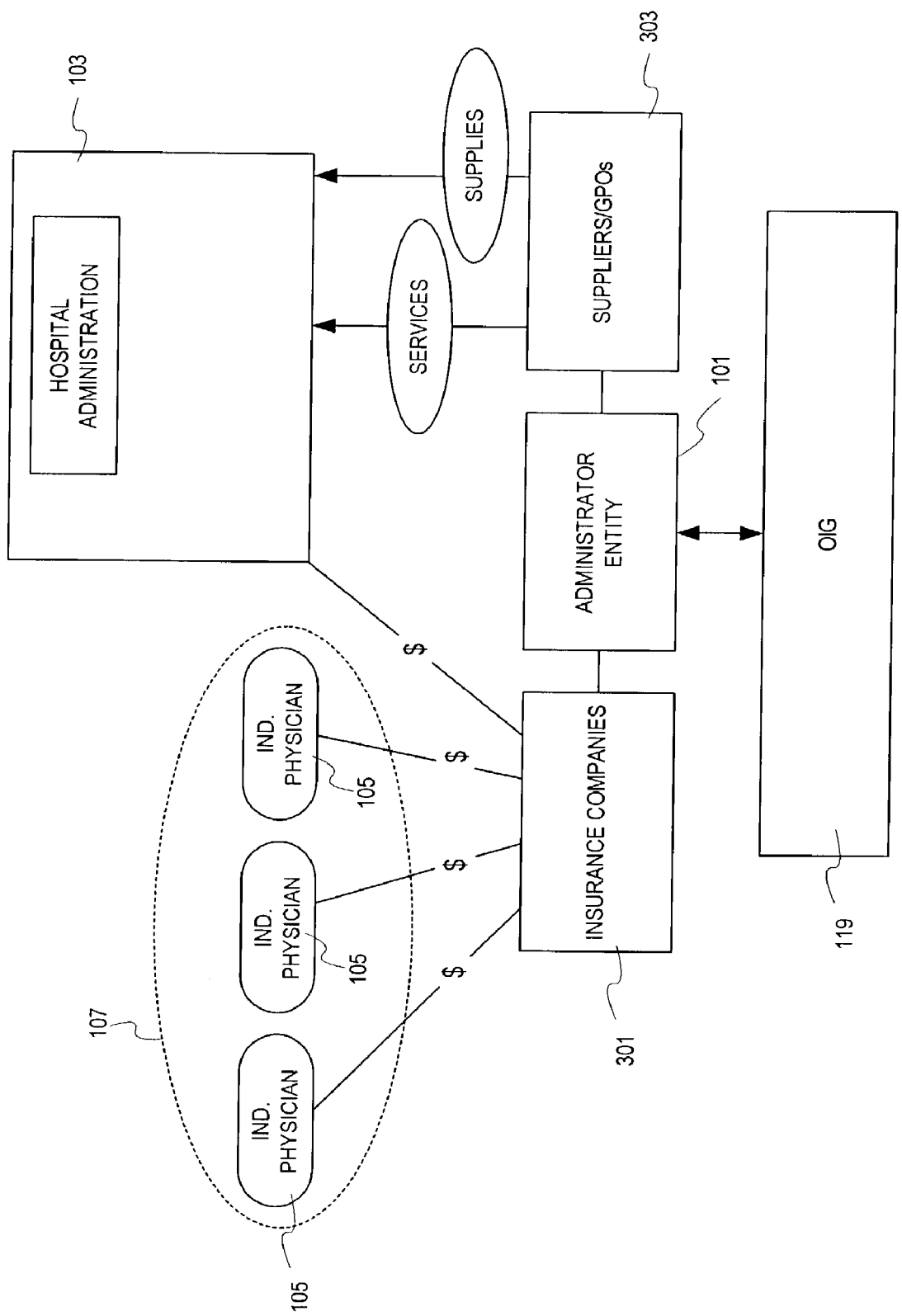
FIG. 3 shows additional relationships that may exist in alternative embodiments of the present invention.

In addition to the structures and relationships shown in FIG. 1, the present invention contemplates various other features illustrated in FIG. 3. In some cases, insurance companies 301 may participate in a given implementation. This may be particularly desirable in cases in which insurance companies 301 reimburse hospitals on a cost-plus-fixed-fee basis, and this form of payment is the majority of the hospital's source of revenue, the present invention may be implemented with the participation of insurance companies. Administrative entity 101 may work with insurance companies 301 to help the hospital benefit from lowering costs and not be penalized by insurance companies 301 lowering reimbursement rates. In this manner, some or all of the cost savings achieved by a cost savings program is retained by hospital 103 to provide hospital 103 an incentive to implement cost savings, and to improve the overall financial performance of hospital 103. Their relationship with a hospital 103 regarding reimbursement rates may be linked to implementation of the present invention and part of the savings shared with them to the extent permitted by governing regulations.

In most cases, implementation of the present invention most likely does not affect the relationship between insurance companies 301 and physicians 105/106. It is expected that the present invention will primarily affect the reimbursement between the hospital 103 and insurance companies 301 for certain activities. However, physicians 105/106 may be party to an overall agreement to implement the present invention that may involve insurance companies 301.

Administrative entity 101 may work with various suppliers 303 and group purchasing organizations (GPOs) to help identify ways to save costs beyond what a given hospital 103 is already able to do on their own. This includes GPOs that provide buying services to hospitals. Administrative entity 101 may introduce new suppliers 303 to the hospital 103 and/or help to negotiate better prices with existing suppliers 303 to help hospitals save money on their purchases.

6. Cost-Saving Measures

Cost-saving measures are well defined steps that when taken will result in a savings and not negatively affect the clinical outcome of the related medical procedures. The alternative steps are FDA approved and considered industry standards. Most measures will directly involve treating patients, although some measures may be indirect.

The active participation of physicians will promote clinical efficacy and maximize savings potential from a technical perspective. Savings typically will be generated through one or more of the following mechanisms, but could be derived from other methods:

Coordination of supply selection to maximize quantity discounts.

Selection of less expensive alternatives in supplies and pharmaceuticals, which are as effective as more expensive counterparts.

Use of reusable items vs. disposable; use of reprocessed single-use devices.

Re-engineering of procedures to minimize excess use of supplies and defining more efficient processes to minimize use of personnel.

Physician-directed competitive bidding to lower prices.

Defining alternative methods to deliver care more efficiently.

An internal process may be created by hospital 103 and/or physicians 105/106 to review and approve measures before implementation. It is expected that each participant will make their own determination before implementing any cost-saving measures and will be responsible for their own choices. Not all proposed measures will be appropriate or necessarily save money in every case. In some cases, minimal training may be required. Physicians 105/106 will decide what is appropriate in each situation and will bear final responsibility for each clinical decision. It is also possible for any given hospital or physician to develop their own cost-saving measures.

7. Establishing Baseline Costs

In order to measure the effectiveness of the program and provide input for financial planning purposes, baseline costs generally are established to determine savings. It is an advantage if cost-savings measures are relatively easy to identify and track. In some cases, the parties may have to negotiate a formula that will estimate the savings. Templates such as spreadsheets may be created to help evaluate the potential for savings at a given hospital 103 and to help establish baseline costs. Administrative entity 101 should coordinate with the hospital's accounting department to define how reports will be generated to determine cost savings and how often. The preferred reporting period is monthly but resources may dictate less often, perhaps quarterly.

Baseline costs will likely need to be updated periodically. In many cases, the cost-saving measure will involve a choice between supplies or agents. The more costly alternative will still be available for comparison to continually establish the baseline cost. If the savings is a result of switching suppliers or negotiated lower prices, the parties will have to continually negotiate to establish a fair ongoing baseline cost assuming the parties had not implemented the cost-saving measure otherwise.

8. Tracking Savings

Each cost-saving measure will require establishing a baseline cost and tracking the results of implementing the cost-saving measure. Generally, the savings generated by any particular activity can be tied to measurable savings per procedure regardless of other clinical issues, such as length of stay or health status of the patient. In some cases, the savings may be estimated based upon mutual agreement, using direct or indirect metrics that are available. A typical example of cost savings would be the choice between one pharmaceutical agent vs. another, both of which provide the same basic clinical outcome, but one is more expensive than the other. The usage of both can be established both before and after implementation of the cost-saving measure. Assuming the less expensive agent is now used more often, the savings can be tracked. The hospital administration should cooperate to generate adequate accounting information and reports such that cost saving calculations are made on a regular basis.

9. Determining Physician Compensation

Under current regulations, payment to physicians 105/106 for services provided should be no more than market rates, be fixed fee and not be contingent or tied to savings achieved, and contract has to be for at least one year. Payments for services to help evaluate, plan and implement cost-saving measures will be dependent upon the situation and complexity for each measure. Clearly, a hospital 103 will not be inclined to enter into an agreement unless there is a reasonable indication that there are sufficient potential savings and the physician 105/106 has indicated a willingness to help achieve those savings.

Payments to physicians for otherwise uncompensated services such as ER on-call should follow the same guidelines as noted in the above paragraph. However, structuring the payments is slightly more complex to ensure payments are not tied to savings. The hospital 103 is free to choose which physicians and how much it can afford to compensate them based upon its financial ability to do so. Projected savings can be taken into consideration by the hospital 103 when it makes this determination.

To validate that a particular implementation follows proper procedures and copies with OIG rules and regulations, it is recommended that oversight and audits be completed by the Program administration or an independent third party as appropriate.

10. Conclusion

Although the invention has been described and illustrated with a certain degree of particularity, it is understood that the present disclosure has been made only by way of example, and that numerous changes in the combination and arrangement of parts can be resorted to by those skilled in the art without departing from the spirit and scope of the invention, as hereinafter claimed. For example, the invention can be implemented with manual systems or computerized systems. The list of cost-saving measures can be expanded as experience is gained. The invention can be implemented with or without the assistance of an administrative group directly between physicians and hospitals. The administrative portion of the system can be complemented with applications that are web-based.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

I claim:

1. A computer-based method for implementing and managing a cost-savings program for a hospital to assist the hospital to budget for compensating physicians for uncompensated or undercompensated services provided at the hospital, wherein the undercompensated services includes services such as emergency room services for which physicians may be compensated at rates substantially below fair market value, comprising:

defining a group of the physicians;

storing a list of the physicians in the group in memory of a computer system;

defining a set of cost-savings measures for selective use in the hospital with input from the physicians on the list, each of the cost-savings measures comprising steps to be performed as part of providing care at the hospital;

storing the cost-savings measures in the memory;

providing an estimated cost saving value for each of the stored cost-savings measures;

operating the computer system to calculate a prospective cost saving total for the hospital, wherein the prospective cost savings total is calculated for an upcoming time period based on a projected implementation of the cost-savings measures by physicians at the hospital and based on the estimated cost saving values associated with the cost-savings measures; and with the computer system, determining and reporting a source of funds for the stored list of the physicians available for the hospital to use in compensating the physicians on the stored list for performing the uncompensated or undercompensated services at the hospital, wherein the source of funds is determined for the upcoming time period based on the prospective cost saving total; and with the computer system determining compensation based on the source of funds for the physicians on the stored list for providing the uncompensated or undercompensated services at the hospital during the time period, wherein the compensation is higher than compensation provided by the hospital for physicians absent from the stored list, wherein the compensation is less than fair market value for corresponding services, and wherein the uncompensated or undercompensated services differ from the cost-savings measures.

2. The method of claim 1, wherein the providing of the estimated cost saving values comprises receiving with the computer system baseline costs associated with the cost-savings measures and using the computer system to determine the estimated cost saving values based upon the received baseline costs.

3. The method of claim 2, further comprising receiving with the computer system a set of measured savings at the hospital determined based on implementation of cost-savings measures and the baseline costs and wherein the determining of the source of funds is performed based on the set of measured savings and based on the prospective cost saving total.

4. The method of claim 1, operating the computer system to determine a compensation for each of the physicians for services associated with selecting and implementing a set of the cost-savings measures.

5. The method of claim 1, wherein the cost-savings measures are selected from the group consisting of coordination of supply selection to maximize quantity discounts, selection of less expensive alternatives in supplies or pharmaceuticals, use of reusable items versus disposable items, re-engineering of procedures to minimize excess use of supplies, competitive bidding to lower prices, and defining alternative methods to deliver care.

6. A computer-based method of providing compensation to hospital-contracted physicians, comprising:

(a) contracting by a hospital with one or more physicians, wherein the hospital provides the one or more physicians with hospital privileges in exchange in part for the one or more physicians providing one or more services at the hospital for which the one or more physicians are uncompensated or compensated at below fair market value;

(b) requesting input from the one or more physicians on how to save costs while maintaining high quality patient care;

(c) defining one or more cost-saving measures for selective use in the hospital based in part on the requested input received from the one or more physicians, wherein each of the cost saving measures comprises steps to be performed as part of providing care at the hospital and differs from the one or more services;

(d) storing in memory an estimated cost saving value for each of the cost saving measures;

(e) requesting voluntary participation in a cost-saving program from the one or more physicians, wherein each of the one or more physicians in the cost-saving program is requested to optionally implement at least one of the cost-saving measures;

(f) running a process on a computer with access to the memory to calculate a prospective cost saving total for the hospital based on the estimated cost saving values and a number of the one or more physicians participating in the cost-saving program, wherein the prospective cost saving total is calculated for an upcoming time period based on a projected number and type of the cost saving measures performed in the hospital during the upcoming time period;

(g) running a process on a computer to determine and report a source of funds available for compensating a physician in the cost-saving program for performing the one or more services, wherein the source of funds is determined for the upcoming time period based on the prospective cost saving total;

(h) during the upcoming time period, the one or more physicians performing the one or more services at the hospital and optionally implementing one or more of the cost saving measures; and (i) determining compensation for each of the physicians in the program for performing the one or more services, wherein the compensation for a physician in the program is a portion of the source of funds and is greater than compensation for a corresponding service for a physician not participating in the program; wherein the compensation is less than or equal to fair market value of the one or more services, and wherein participation in the cost-saving program is required to receive the compensation.

\* \* \* \* \*